US006197299B1

(12) United States Patent
Dohlsten et al.

(10) Patent No.: US 6,197,299 B1
(45) Date of Patent: *Mar. 6, 2001

(54) ANTIBODY CONJUGATES

(75) Inventors: Mikael Dohlsten, Lund; Eva Åkerblom, Uppsala; Peter A. Lando, Malmö; Terje Kalland, Löddeköpinge; Gunnar Hedlund, Lund, all of (SE)

(73) Assignee: Pharmacia & Upjohn AB, Stockholm (SE)

( * ) Notice: Subject to any disclaimer, the term of this patent is extended or adjusted under 35 U.S.C. 154(b) by 0 days.

This patent is subject to a terminal disclaimer.

(21) Appl. No.: 09/154,310

(22) Filed: Sep. 16, 1998

Related U.S. Application Data

(63) Continuation of application No. 08/485,706, filed on Jun. 7, 1995, now Pat. No. 5,858,363, which is a continuation of application No. 08/339,279, filed on Nov. 8, 1994, now abandoned, which is a continuation of application No. 07/961,937, filed on Jan. 14, 1993, now abandoned, which is a continuation of application No. PCT/SE91/00496, filed on Jul. 16, 1991.

(30) Foreign Application Priority Data

Jul. 20, 1990 (SE) .................................................. 9002484
Jul. 20, 1990 (SE) .................................................. 9002489

(51) Int. Cl.[7] ...................... A61K 39/395; A61K 39/385; A61K 39/40; C07K 16/00

(52) U.S. Cl. .................................... 424/183.1; 424/178.1; 424/179.1; 424/193.1; 424/277.1; 424/165.1; 424/237.1; 530/391.1; 530/391.7; 530/391.9

(58) Field of Search ............................. 424/183.1, 178.1, 424/179.1, 193.1, 277.1, 165.1, 237.1, 801, 134.1; 530/391.1, 391.7, 391.9, 567; 435/69.1

(56) References Cited

U.S. PATENT DOCUMENTS

| | | |
|---|---|---|
| 3,627,644 | 12/1971 | Okamoto et al. . |
| 4,237,224 | 12/1980 | Cohen et al. . |
| 4,268,434 | 5/1981 | Higerd et al. . |
| 4,681,870 | 7/1987 | Balint, Jr. et al. . |
| 4,699,783 | 10/1987 | Terman et al. . |
| 4,980,160 | 12/1990 | Goldberg et al. . |
| 5,091,091 | 2/1992 | Terman . |
| 5,858,363 * | 1/1999 | Dohlsten et al. ................. 424/183.1 |

FOREIGN PATENT DOCUMENTS

| | | |
|---|---|---|
| 2828947 | 7/1977 | (DE) . |
| 355047 | 7/1989 | (EP) . |
| 8702602 | 10/1987 | (WO) . |
| 9100342 | 6/1989 | (WO) . |
| 9000592 | 9/1990 | (WO) . |
| 9201470 | 7/1991 | (WO) . |

OTHER PUBLICATIONS

Todd et al., Toxic Shock Syndrome Associated with Phage–Group I Staphylococci Lancet 2: 116–120 (1978).
Shands et al., Toxic Shock Syndrome in Menstruating Woman: Association with Tampon Use and *Staphylococcus Aureus* and Clinical Features in 52 Cases New Engl, J. Med. 303 1436–1441 (1980).
Fisher et al., Cardio–respiratory Failure in Toxic Shock Syndrome: Effect of Dobutamine Critical Care Medicine 13: 160–165 (1985).
Bergdoll et al., A New Staphylococcus Enterotoxin, Enterotoxin F, Associated with the Toxic Shock Syndrome *Staphylococcus aureus* Isolates Lancet 2 1017–1021 (1981).
Willoughby et al., The Toxic Shock Syndrome and Streptococcal Pyrogenic Exotoxins Ann. Int. Med. 98: 559 (1983).
Cone et al., Clinical and Bacteriological Observations of a Toxic Shock–Like Syndrome due to Streptococcus Pyrogenes New Engl. J. Med. 317: 146–148 (1987).
Stevens et al., Severe Group A Streptococcal Infections Associated with a Toxic Shock–like Syndrome and Scarlet Fever Toxin A New Engl J. Med 32: 321: 1–7 (1989).
Schilievert, PM Staphylococcal Enterotoxin B and Toxic Shock Syndrome Toxin–1 are Significantly Associated with Non–Menstrual TSS Lancet 1: 1149–1150 (1986).
Johnson et al., Mol. Gen. Genet. 203, 354 to 356 (1986).
Borja et al., Biochemistry vol. 6, No. 5, pp. 1467 to1473, 1967.
Elsberry et al., Hemodynamics of Staphylococcal B Enterotoxaemia and Other Types of Shock in Monkeys J. Applied Physiology 27 164–169.
Liu et al., Cardiovascular and Vomiting Responses to a Lethal Intravenous Dose of Staphyloenterotoxin A in Rhesus Monkeys J Med Primatol. 5: 353–359 (1976).
Acolla RJ et al., J. Exp. Med. 157: 1053–1058 (1983).
Kravath et al., Gamma Ray–induced Loss of Expression of HLA and Glyoxalase I Alleles in Lymphoblastoid Cells Proc. Natl. Acad. Sci. USA 77: 4251–4255 (1980).
Acolla et al., J. Exp. Med. 162: 1117–1133 (1985).
Acolla et al., J. Exp. Med. 164: 369–374 (1986).

(List continued on next page.)

*Primary Examiner*—Jyothsna Venkat
*Assistant Examiner*—P Ponnaluri
(74) *Attorney, Agent, or Firm*—Fulbright & Jaworski L.L.P.

(57) ABSTRACT

A soluble antibody conjugate comprising an antibody linked to a structure which is recognized by T-cells and has the ability to direct T-cells to lyse the target cell, which is recognized by the antibody. The conjugate is characterized by the structure being a superantigen. One important mode is a method for the lysis of target cells, wherein the target cells are contacted with a target cell lysis effective amount of the conjugate. The method of lysis is part of a potent treatment regime for cancer, autoimmunity, parasitic infestations and fungal, viral and bacterial infections. The specification also describes modes such as the synthesis of the conjugate and pharmaceutical compositions and their manufacture.

32 Claims, 3 Drawing Sheets

OTHER PUBLICATIONS

Acolla et al., Proc. Natl. Acad. Sci. USA 82: 5145–5149 (1985).
Shoemaker et al., Development of Human Tumour Cell Line Panels for use in Disease–Oriented Drug Screening in T. Hall editor Prediction of Response to Cancer Therapy Alan Liss N.Y. pp. 265–286 (1988).
Paull K.D. et al., J. Natl. Cancer Inst. 81: 1088–1092 (1989).
Alley M.C. et al., Cancer Res. 48: 589–601 (1988).
Scudiero D.A. et al., Cancer Res. 48: 4827–4833 (1988).
Developmental Therapeutics Program Division of Cancer Treatment, National Cancer Institute Proceedings of Workshop on "Selection, Characterisation and Quality Control of Human Tumour Cell Lines from the NCI's New Drug Screening Program" Bethesda, MD May 27–28, 1–73 (1987).
Boyd M.R. Status of NCI preclinical antitumour drug discovery screen in De Vita V.T., Hellman S., Rosenberg S.A., eds Cancer: Principles and Practice of Oncology Updates, vol. 3, No. 10, Lippincott, Philadelphia 1–12 (1989).
Rooney C., et al., J. Natl. Cancer Inst. (1986).
Sausville E.A. in Anticancer Drug Development Guide: Preclinical Screening, Clinical Trials and Approval B. Teicher editor, Human Press, Totowa, N.J.
D. Terman et al., "Preliminary Observations of the Effects on Breast Adenocarcinoma of Plasma Perfused Over Immobilized Protein A," New Eng. J. Med., 305:1195–1200 (1981).
F. Chu et al., "Purification and Characterization of Staphylococcal Enterotoxin A," Biochem., 5:3281 (1966).
M. Bergdoll et al., Identification of a New Enterotoxin as Enterotoxin C, J. Bacteriol., 90:1481 (1965).
C. Borja and M. Bergdoll, "Purification and Partial Characterization of Enterotoxin C Produced by *Staphylococcus aureus* Strain 137," Biochem., 6:1467 (1967).
R. Avena and M. Bergdoll, "Purification and Some Physicochemical Properties of Enterotoxin C, *Staphylococcus aureus* Strain 361," Biochem., 6:1474 (1967).
E. Schantz et al., "Purification and Some Chemical and Physical Properties of Staphylococcal Enterotoxin A." Biochem., 11:360 (1972).
E Schantz et al., "Purification of Staphylococcal Enterotoxin B," Biochem., 4:1011 (1965).
H–C. Chang and M. Bergdoll, "Purification and Some Physicochemical Properties of Staphylococcal Enterotoxin D," Biochem., 18:1937 (1979).
C. Borja et al., "Purification and Some Physicochemical Properties of Staphylococcal Enterotoxin E," J. Biol. Chem., 247:2456 (1972).
M. Dayhoff (ed.), Data Section, in *Atlas of Protein Sequence Structure* 5:D227, National Biomedical Research Foundation, Washington, D.C. (1972).
I. Huang and M. Bergdoll, "The Primary Structure of Staphylococcal Enterotoxin B," J. Biol. Chem., 245:3493 (1970).
M. Bergdoll et al., "Enterotoxin Synthesis by the Staphylococci,"In *Recent Advances in Staphylococcal Research* (W.W. Yotis, ed.), Ann. N.Y. Acad. Sci., 236:307.
J. Iandolo, "Genetic Analysis of Extracellular Toxins of *Staphylococcus aureus*," Ann. Rev. Microbiol., 43:375 (1989).
M. Bergdoll et al., "Staphylococcal Enterotoxin B, III. The Physicochemical Properties and the N– and C–Terminal Amino Acid Sequences," Arch. Biochem. Biophys., 112:104 (1965).
I. Huang et al., "Amino Acid Composition and Terminal Amino Acids of Staphylococcal Enterotoxin C," Biochem., 6:1480 (1967).
M. Bergdoll et al., "Chemistry of the Staphylococcal Enterotoxins," J. Agric. Food Chem., 22:9 (1974).
D. Blomster–Hautamaa et al., "Preparation of Toxic Shock Syndrome Toxin–1," Methods in Enzymology 165:37 (1988).
M. Bergdoll et al., "Identification of Enterotoxin E," Infect. Immun., 4:593 (1971).
M. Bergdoll, "Enterotoxins," in *Staphylococci and Staphylococci Infections* (C.S.F. Easmon and C. Adlam, eds.), pp. 559–598 (1983).
J. Freer and J. Arbuthnott, "Toxins of *Staphylococcus aureus*," Pharmac. Ther., 19:55 (1983).
L. Johnson et al., "Streptococcal Pyrogenic Exotoxin Type A (scarlet fever toxin) is related to *Staphylococcus aureus* Enterotoxin B," Mol. Gen. Genet., 203:354 (1986).
W. Pearson and D. Lipman, "Improved Tools for Biological Sequence Comparison," Proc. Natl'l. Acad. Sci. USA, 85:2444 (1988).
J. Lipman and W. Pearson, "Rapid and Sensitive Protein Similarity Searches," Sci., 227:1435 (1985).
C. Janeway, Jr. et al., "T–Cell Responses to Mls and to Bacterial Proteins that Mimic its Behavior," Immunol. Rev., 107:61–88.
J. Yagi et al., "Bacterial Proteins That Mediate the Association of a Defined Subset of T Cell Receptor:CD4 Complexes With Class II MHC," J. Immunol., 144:892–901.
H. Stewart et al., in *Atlas of Tumor Pathology*, Armed Forces Institute of Pathology, Washington, D.C., pp. 38, 355 (1959).
J. Kidd et al., "A Transplantable Rabbit Carcinoma Originating in a Virus–Induced Papilloma and Containing the Virus in Masked or Altered Form," J. Exp. Med., 71:813–838 (1940).
T. Maniatis et al., *Molecular Cloning: A Laboratory Manual*, Cold Spring Harbor Laboratory, New York (1982).
J. Betley and J. Mekalanos, "Nucleotide Sequence of the Type A Staphylococcal Enterotoxin Gene," J. Bacteriol., 170:34 (1987).
I. Huang et al., "Complete Amino Acid Sequence of Staphylococcal Enterotoxin A," J. Biol. Chem., 262:7006 (1987).
M. Betley et al., "Staphylococcal Enterotoxin A Gene is Associated With a Variable Genetic Element," Proc. Natl. Acad. Sci. USA 81:5179 (1984).
M. Gaskill and S. Khan, "Regulation of the Enterotoxin B Gene in *Staphylococcus aureus,*" J. Biol. Chem., 263:6276 (1988).
C. Jones and S. Khan, "Nucleotide Sequence of the Enterotoxin B Gene from *Staphylococcus aureus,*" J. Bacteriol., 166:29 (1986).
I. Huang and M. Bergdoll, "The Primary Structure of Staphylococcal Enterotoxin B," J. Biol. Chem., 245:3518 (1970).
G. Bohach and P. Schlievert, "Expression of Staphylococcal Enterotoxin $C_1$ in *Escherichia coli*," Infect. Immun., 55:428 (1987).
G. Bohach and P. Schlievert, "Nucleotide Sequence of the Staphylococcal Enterotoxin $C_1$ Gene and Relatedness to Other Pyrogenic Toxins," Mol. Gen. Genet., 209:15 (1987).
J. Couch et al., "Cloning and Nucleotide Sequence of the Type E Staphylococcal Enterotoxin Gene," J. Bacteriol., 170:2954 (1988).

B. Krieswirth et al., "The Toxic Shock Syndrome Exotoxin Structural Gene is Not Detectably Transmitted by a Prophage," Nature 305:709 (1983).

J. Cooney et al., "Molecular Cloning and Genetic Analysis of the Determinant for Gamma–Lysin, a Two–component Toxin of *Staphylococcus aureus*," J. Gen. Microbiol., 134:2179 (1988).

M. Friedman et al., "Induction of Mutants of *Staphylococcus aureus* 100 With Increased Ability to Product Enterotoxin A," J. Bacteriol., 106:289 (1971).

D. Terman, "Staphylococcal Protein A in Neoplastic Disease," J. Biol. Response Modifiers 3:316 (1984).

D. Terman and J. Bertram.,"Antitumor Effects of Immobilized Protein A and Staphylococcal Products: Linkage Between Toxicity and Efficacy, and Identification of Potential Tumoricidal Reagent," Eur. J. Cancer Clin. Oncol., 21:1115 (1985).

D. Terman, "Immunoadsorbents in Autoimmune and Neoplastic Diseases," Plasma Ther. Transfus. Technol., 4:415 (1983).

D. Terman, "Protein A and Staphylococcal Products in Neoplastic Disease," CRC Crit. Rev. Oncol./Hematol., 4:103 (1985).

D. Terman, "Immobilized Enzymes and Cells," in *Methods in Enzymology*, vol. 137 (K. Mosbach, ed.), Academic Press, San Diego, pp. 496–515 (1988).

J. Mikolàšek, "Direct Evidence for Rejection of Tumour Allografts in *S. pyogenes* Toxins–Treated Mice Correlated with Antistreptolysin O Level in Serum," Neoplasma 19:507 (1972).

O. Shcheglovitova et al., Eksp Onkol., 9(1):28–30 (1987), cited in: Biol. Abstr., 84(5):AB–685, Ref. 48345 (1987); O.N. Shcheglovitova et al., Eksp Onkol., 11(2):54–57 (1989), cited in: Biol. Abstr., 88(8):AB–700, Ref. 87362 (1989); and O.N. Shcheglovitova et al., Eksp Onkol., 11(1):73–74 (1989), cited in: Biol. Abstr., 88(7):AB–639, Ref. 75810 (1989).

P. Garcia–Peñarrubia et al., "Selective Proliferation of Natural Killer Cells Among Monocyte–Depleted Peripheral Blood Mononuclear Cells as a Result of Stimulation with Staphylococcal Enterotoxin B," Infect. and Immun., 57:2057 (1989).

E. Carswell et al., "An Endotoxin–induced Serum Factor That Causes Necrosis of Tumors," Proc. Nat. Acad. Sci. USA 72:3666 (1975).

D. Fast et al., "Toxic Shock Syndrome–Associated Staphylococcal and Pyrogenic Toxins Are Potent Inducers of Tumor Necrosis Factor Production," Infect. Immun., 57:291 (1989).

C. Platsoucas et al., "Immunomodulation of Human Leukocytes by Staphylococcal Enterotoxin A: Augmentation of Natural Killer Cells and Induction of Suppressor Cells," Cellular Immunol., 97:371 (1986).

K. Newell et al., "In vivo T–cell Activation by Staphylococcal Enterotoxin B Prevents Outgrowth of a Malignant Tumor," Proc. Natl. Acad. Sci. USA 88:1074 (1991).

J. Kappler et al., "Vβ–Specific Stimulation of Human T Cells by Staphylococcal Toxins," Science 244:811–813 (1989).

H. Schrezenmeier and B. Fleischer, "Mitogenic Activity of Staphylococcal Protein A is Due to Contaminating Staphylococcal Enterotoxins," J. Immun. Meth., 105:133 (1987).

J. Sjöquist et al., "Protein A Isolated From *Staphylococcus aureus* After Digestion With Lysostaphin," Eur. J. Biochem., 29:572 (1972).

J. Balint, Jr. et al., "Detection, Isolation and Characterization of Staphylococcal Enterotoxin B in Protein A Preparations Purified by Immunoglobulin G Affinity Chromatography," J. Immun. Meth., 116:37 (1989).

* cited by examiner

ANTIBODY CONJUGATES

This application claims priority as a continuation of U.S. application Ser. No. 08/485,706, filed Jun. 7, 1995, U.S. Pat. No. 5,858,363, which is a continuation of U.S. application Ser. No. 08/339,279, filed Nov. 8, 1994, now abandoned, which is a continuation of U.S. application Ser. No. 07/961,937, filed Jan. 14, 1993, now abandoned, which is Continuation of PCT application number PCT/SE91/00496, international filing date Jul. 16, 1991, which is based upon Swedish patent application numbers 9002484-5 and 9002479-5, both filed Jul. 20, 1990.

The present invention concerns antibody conjugates which are capable of activating cytotoxic T-cells (CTLs). The conjugates are useful for destroying undesired cells that are associated with i.a. cancer forms, autoimmune processes, parasitic infestations and bacterial, viral and fungal infections.

BACKGROUND OF THE INVENTION

Attempts have been made over the past years to use antibodies in combination with agents that directly exert a toxic effect on target cells (cytotoxic agents, cytotoxins) in order to provide a selective action on target cells and to prevent and minimize the non-specific effect on other cells. The combinations suggested have ranged from covalently bonded complexes using linkage-providing molecules and non-covalently bonded complexes to simple mixings (e.g. Ghose et al., J. Natl. Cancer Inst. 61(1979)657–676 and Carlsson et al., Biotechnology 7(1989)567–73). Suggested cytotoxins have been i.a. diphteria toxin, ricin, subunit A of ricin, gelonin, and Pseudomonas aeruginosa exotoxin A (Takeda Chemical Ind., EP-A-336,405 and Pastan et al., WO-A-88/00703, both of which have been cited in connection with the priority application, SE-9002479).

With the advent of the hybridoma technology and the accompanying availability of monoclonal antibodies, it has been feasible to use the concept of complexes between antibodies and cytotoxic agents to more specifically direct the cytotoxic agents to the intended target cell population.

In view of the recognized damaging effect of cytotoxic agents on other cells than target cells, one has suggested to replace the cytotoxic agents with immune stimulators that trigger T-lymphocytes and activate CTLS. Specific proposals have been concerned with antibodies conjugated to (i) antibodies that are directed against a T-cell receptor or compounds that are able to bind to a T-cell receptor (Mass. Inst. Techn., EP-A1-180,171);

(ii) compounds, such as antigens, mitogens, other foreign proteins, and peptides that activate cytotoxic T-cells (Neorex Corp., EP-A1-334,300);

(iii) MHC antigens, (Behringwerke AG, EP-A1-352,761);

(iv) antigens against which the individual to be treated has immunity, (Med. Res. Counc. WO-A-90/11779 (publ. 1990-10-18)); and (v) an unnamed bacterial enterotoxin (Ochi and Wake, UCLA-symposium: Cellular Immunity and the Immunotherapy of Cancers, Jan. 27–February 3, 1990, Abstract CE 515. page 109).

However, the immune stimulators suggested hitherto have been either too specific or too general in their action. For instance classical antigens activate only about 1 out of $10^5$ T-cells while mitogens are potentially capable of activating a majority of the T-cells.

It has been recognized that certain-agents mediate activation of a-moderate ratio of T-cells; i.e. they activate T-cells at a relatively high frequency, but far from 100% (Fleischer et al., J. Exp. Med. 167(1988)1697–1707; and White et al., Cell 56(1989)27–35, both articles being incorporated by reference). This type of agents are more effective activators than classical antigens and they accordingly have been named superantigens (for a review see Kappler and Marrack, Science 248:705, (1990)). It has further been demonstrated (Dohlsten et al., Immunol. 71(1990)96–100; and Hedlund et al., Cell. Immunol 129(1990)426–34, both articles being incorporated by reference) that the superantigens known so far have the capacity to bind to MHC Class II molecules on target cells and activate cytotoxic T-cells bearing the proper T-cell receptor V beta chain. The published data indicate that the MHC binding is a prerequisite for T-cell binding and activation to occur. It can not be excluded that in the future superantigens will be found that act through a T-cell receptor V alpha chain or other surface structures only found on subpopulations of T-cells.

The immunomodulatory effect of the superantigen Staphylococcus enterotoxin A(SEA) has also been described by Platsoucas et al (Cell Immunol. 97(1986)371–85).

Most of the presently known superantigens have earlier been recognized as toxins and all of them have been of microbial origin. Staphylococcal enterotoxins for instance are enterotoxic and activate T-cells, and the two effects are discernible from each other (Fleischer et al., Cell. Immunol. 118(1989)92–101; Alber et al., J. Immunol 144(1990) 4501–06; and Infect. Immun. 59(1991)2126–34).

It has previously been suggested to use superantigens in order to direct CTL mediated lysis of cells carrying MHC Class II antigens (Pharmacia AB, WO-A-91/04053, publ. 1991-04-04). Wo-A-91/04053 covers, but does not explicitly mention, superantigens that are incorporated into covalent immunoconjugates.

Cells lacking MHC Class II or expressing marginal amounts of MHC Class II proteins do, however, not bind sufficient amounts of superantigens in order to efficiently direct lysis of them by CTLS. Thus due to the general abundance of cells carrying MHC Class II antigens and the non-abundance of MHC Class II antigens on most tumour cells, superantigens should be of low value for the specific killing of such unwanted cells.

However, we have found that a specific cell-killing effect mediated by CTLs can be achieved with superantigens, if they are covalently linked to an antibody directed against an epitope that is specific for the cell to be killed. The activation of the immune system may induce target cells lacking MHC Class II antigens to express them, which may potentiate the desired lytic effect.

SUMMARY OF THE INVENTION

The present invention provides novel antibody conjugates (i) comprising (1) an antibody directed against target cells, and (2) a superantigen, i.e. a structure that is recognized (interact with or bind to) and activate T-cells, in particular CTLs;

(ii) methods for destroying target cells, in particular in connection with therapeutical treatment methods contemplated on mammals, and for specific activation of T-cells, such as CTLS;

(iii) method of synthesis for the conjugates; and (iv) pharmaceutical compositions containing the conjugates and preparation methods for the compositions.

The methods for destroying target cells encompasses therapeutic treatment methods for cancer, autoimmunity, viral infections, bacterial infections, fungal infections, parasitic infestations and other diseases in which the objective is to kill certain cells with a high degree of accuracy. The conjugates of the invention may be used for the manufacture of pharmaceutical compositions intended to be used for destroying target cells associated with the diseases just given. The individuals to be treated are normally animals, primarily human beings.

DETAILED DESCRIPTION OF THE INVENTION

Superantigen Dart of the Conjugate

Figure 1A:
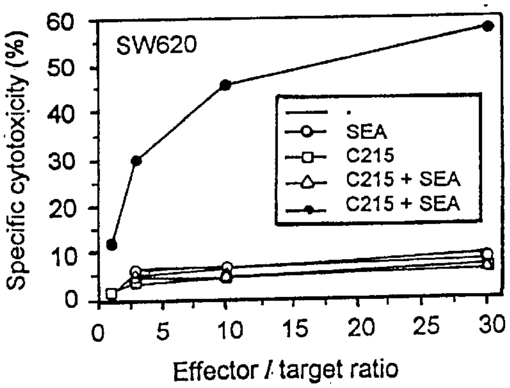
FIG. 1 shows SEA-C215 mAb conjugate directing CTLs against MHC class II colon carcinoma cells.
Figure 1B:
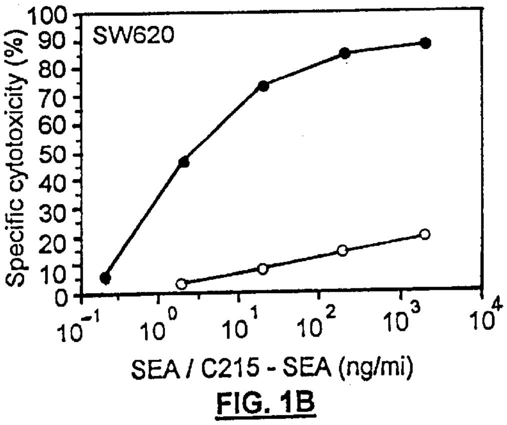
Figure 1C:
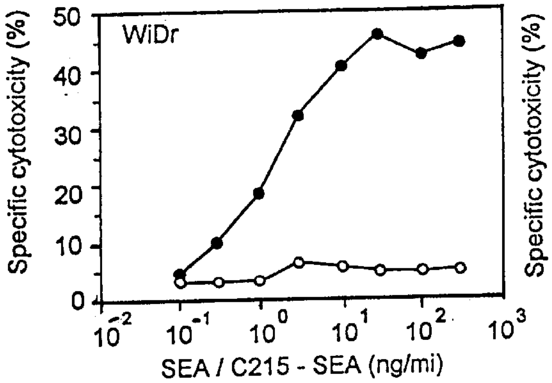
Figure 1D:
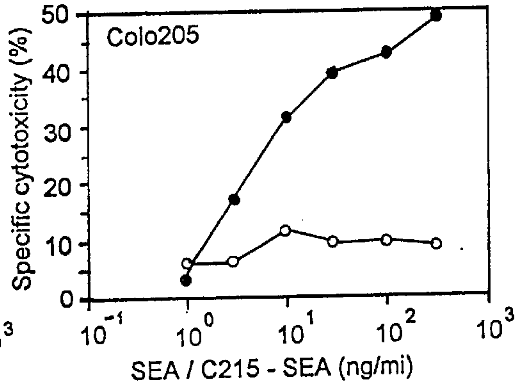
Figure 1E:
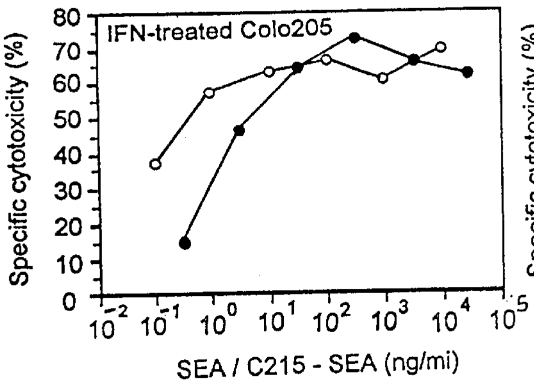
Figure 1F:
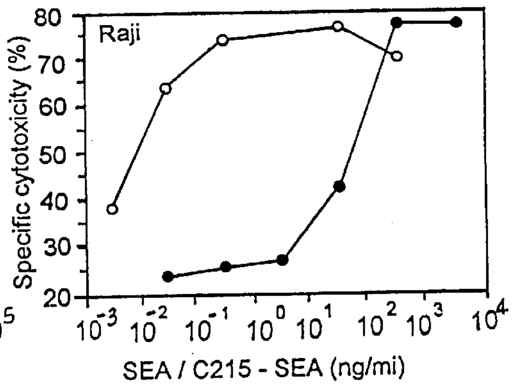

The novel antibody conjugates are characterized by the structure that is recognized by the T-cells being a superantigen. The conjugates are normally soluble at physiological pH and in vitro they are soluble in serum.

Preferred superantigens are selected from the group of staphylococcal enterotoxins (SEs), such as SEA, SEB, SEC, SED and SEE, toxoids, active fragments or peptides thereof and other substances having essentially the same mode of action for activating CTLS. The superantigens may include other microbial products (bacterial as well as viral), such as products from staphylococcal strains, e.g. Toxic Shock syndrome toxins (TSST-1), from Streptococci, e.g. pyrogenic exotoxin A, and bacterial exoproteins and proteins produced by mycoplasma arthridis, which have similar capacity to interact with T-cells in the same way as superantigens do. Superantigens may be obtained by culturing of their natural producers or of genetically engineered cells (recombinant techniques) or potentially also by synthetic peptide synthesis. A superantigen to be used in the invention should, when applied to the experimental model presented in this specification, exert effects in analogy with what we present in the experimantal part of this specification.

The preferred superantigens have the potential ability to bind to about 1–40% of the isoforms of a polymorphic T-cell surface protein associated with the activation of CTLS, preferably the T-cell receptor V beta chain.

The Antibody Part of the Conjugate

The antibody is preferably a monoclonal antibody (mab) although polyclonals may be used as long as they provide a sufficiently narrow specificity. The expression antibody refers to antibodies in general and thus encompasses antibody active fragments, and other molecules mimicrying the binding ability of an antibody, providing they have the appropriate specificity, avidity and affinity for the target cell in question. This includes genetically engineered (recombinantly produced) antibodies and antibody derivatives or other similarly binding structures. In the one embodiment the antibody is specific for an antigenic determinant on tumour cells, for instance a colon carcinoma associated determinant (epitope, structure). It is also conceivable that the antibody may be specific for an antigenic determinant on cells responsible for autoimmunity, virus infected cells, bacteria, parasites or fungi or other un-wanted cells. Depending on the efficiency of the conjugate, the antibody may be directed to an antigen that will internalize the antibody after binding, although it is believed that such antibody specificities are not preferred.

Monoclonal antibodies studied in connection with this invention are the C215 antibody directed against an antigen in the GA-733 family (see for instance EP-A-376,746 and references cited therein and Larsson et al., Int. J. Canc. 42(1988)877–82), the C242 antibody (Larsson et al., Int. J. Canc. 42(1988)877–82) and the Thy-1.2 antibody (mab C, Opitz et al., Immunobiol. 160(1982)438-). It is conceivable that mabs having specificities for other target cell surface structures will be useful. The preparation of monoclonals directed against epitopes unique for selected target cells are wellknown in art. See for instance the above-mentioned publications. Expressions, such as monoclonal antibodies directed against the C242 epitope or the C215 epitope, cover antibodies reacting with cross-reacting epitopes.

Of the three monoclonals tested so far C215-conjugates most probably will be of minor importance because they react with an epitope on a tumour antigen that too frequently is expressed on normal cells. C242-conjugates appear to be better based on specificity data although our results indicate that they may require higher dosages. Mab C directed against Thy-1.2 will probably be of low value for targeting human cancer cells because the Thy-1.2 antigen is specific for a non-human mammalian tumour cell.

A hybridoma cell line producing the C242 monoclonal antibody has been deposited on Jan. 26, 1990 under number ECACC 90012601 at European Collection of Animal Cell Culture, Porton Down, Salisbury, Wilts, U.K.

The Structure Linking the Superantigen to the Antibody

In the preferred conjugate of the invention the superantigen is covalently coupled to the antigen through a covalently linkage. (—B—). If it is important that the conjugate will not decompose when administered to the cells to be killed, for instance to an animal, the linkage should be essentially metabolically stable for a sufficient period of time for the effect to be achieved. Furthermore, it is of advantage that the linkage as such does not give rise to immunological reactions itself. In general the linkage shall be inert in the sense that the conjugate retains an efficient target cell binding specificity (anti-tumour, antiviral etc.) and an efficient capability of activating cytotoxic T-cells.

In the scientific as well as in the patent literature several functional groups have been suggested in linkage structures of immunoconjugates. Accordingly the linkage —B— in our novel conjugates may contain structures selected from he group consisting of (i) amides and hydrazides (amides=—$CONR_1$— or —$NR_1CO$—, where each of the free valencies binds to a saturated carbon atom, and $R_1$ may be hydrogen or an alkyl substituent such as lower alkyl ($C_{1-6}$) or the alpha-N-substituent of a naturally occurring alpha amino acid, preferably a hydrophilic amino acid, and hydrazides=—CONHNH— or —NHNHOC— where each of the free valencies binds to a saturated carbon atom);

(ii) thioether and disulfide (—$S_r$— where each of the free valencies binds directly to a saturated carbon atom, respectively, and S is a sulphur atom, and r an integer 1 or 2);

(iii) straight, branched or cyclic hydrocarbon chains which are saturated and which possibly may be substituted with one or more hydroxy or amino groups;

(iv) ether (—O—, where each of the free valencies binds directly to a saturated carbon-atom); and (V) primary amine or disubstituted hydrazine (—NH— or —NH—NH—, respectively, where each of the free valencies binds directly to a saturated carbon atom).

The length of the bridge should be within the ranges normally contemplated within the technical field, i.e. shorter than 180 atoms, such as <100 atoms, but longer than 3–6, preferably longer than 16 atoms.

The preferred linkage is hydrophilic and should not contain any aromatic ring. Preferred hydrophilic structures that may form part of the linkage —B— are: (i) polypeptide chains of the naturally occurring hydrophilic alpha amino acids (e.g. asparaginic acid and its amide, glutaminic acid and its amide, lysine, arginine, glycine, threonine, serine and possibly also histidine); (ii) oxaalkylene chains such as $(—O(CH_2)_n)_{n'}—$ where n is an integer 2–5, preferably 2–3, and n' may be an integer 1–20; and (iii) —S— (thioethers), —O— (ethers) and unsubstituted amides (—CONH—) all of which being linked to short unsubstituted hydrocarbon chains ($C_{1-4}$), preferably containing 1 or 2 carbon atoms.

Hydrophilic amino acids may be present in hydrophilic structures of the type $(F-(Pro)_n)_mF$, wherein F represents an amino acid sequence, preferably 4–8 residues, in which each amino acid is individually selected from serine, glycine and threonine, m is an integer 1–4 and n an integer 4–8 (Cetus Corp., WO-A-85/03508).

The linkage —B— may be attached either at specific locations in the antibody or superantigen part of the conjugate or at random. Potential locations are an amino terminal, a carboxy terminal and a lysine residue (omega amino group). If the antibody or superantigen carries a thiol group or disulfide group (cystine or cysteine, respectively) these groups may also be used for covalently coupling, unless they are not essential for the activity of the active parts of the conjugate. When present, carbohydrate structures can be oxidized to aldehyde groups that in turn may used for linking to the other moiety of the conjugate (cf. Cetus Corp., EP-A-240,200).

The conjugate of the invention should not contain any significant amounts of ester bonds and labile amide bonds, in particular not formed with tyrosine and histidine residues, respectively. If such bonds have been formed during the synthesis they can be removed by use of hydroxylamine (Endo et al., Cancer Res. 48(1988)3330–3335).

The number of superantigen moieties that may be present per antibody active moiety is normally 1–5, preferably 1 or 2.

In one of the preferred modes the conjugate substance shall be substantially uniform with regard to superantigen per antibody, and/or employed binding positions in the superantigen and antibody moieties, respectively, and/or linkage —B— etc. In other words all the individual conjugate molecules in conjugate substance should be the same in regard to these variables.

The substance should be essentially free from unconjugated antibodies or unconjugated superantigens.

The exact ratio superantigen to antibody, linkage structure etc. for the optimal conjugate will depend on the selected monoclonal (including class, subclass, producing clone, specificity) and selected superantigen. The experimental models given in this specification will enable the screening for optimal parameters also for other superantigens and other antibodies.

According to the embodiment of the invention studied most extensively up to the filing date, the linkage —B— comprises the structure $$—S_rRCONHCH_2CH_2(OCH_2CH_2)_nO(CH_2)_mCOY— \quad (I)$$

The free valencies in formula I link to the active parts, respectively. This takes place either directly or through further divalent inert structures that are comprised within the bridge —B—.

n is an integer >0, e.g. 1–20, preferably 2 or >2 and in many cases <10. m is 1 or 2.

S is a sulphur atom and binds directly to a saturated carbon atom at each of its valencies ($—S_r$=a thioether or a disulfide). r is an integer 1 or 2.

Y is —NH—, —NHNH— or —NHN═CH— that at their left ends bind to the CO group shown in the right terminal in formula I and at their right ends to a saturated carbon atom or to a carbonyl group (only when Y equals —NHNH—).

R is preferably alkylene (having 1–4 carbon atoms, often 1 or 2 carbon atoms), that possibly is substituted with one or more (1–3, in the preferred case <2) hydroxy (OH) groups.

Preparation of the Antibody-superantigen Conjugate

The antibody conjugates of the present invention can be obtained by enriching and purifying them from culture media of cells producing them, or from other media in which they have been synthesized.

The synthesis of our novel conjugates may be accomplished by techniques known in the art for conjugate synthesis, i.e. genetic engineering (recombinant techniques) or via the appropriate antibody and superantigen by classical coupling reactions at appropriate functional groups. The functional groups present in proteins and normally utilized are:

(i) Carbohydrate structures. This structure may be oxidized to aldehyde groups that in turn are reacted with a compound containing the group $H_2NNH—$ to the formation of a —C═NH—NH— group.

(ii) Thiol group (HS—). The thiol group may be reacted with a compound containing a thiol-reactive group to the formation of a thioether group or disulfide group. Free thiol groups of proteins are present in cystine residues and may be introduced onto proteins by thiolation or splitting of disulfides in native cysteine residues.

(iii) Free amino groups ($H_2N—$) in amino acid residues. An amino groups may be reacted with a compound containing an electrophilic group, such as an activated carboxy group, to the formation of an amide group. The free amino group preferably is an amino terminal or the omega amino group of a lysine residue.

(iv) Free carboxy groups in amino acid residues. A carboxy group may be transformed to a reactive (activated) carboxy group and then reacted with a compound containing an amino group to the formation of an amide group. However, precautions must then be taken to minimize amide formation with the amino groups that mostly are present together with carboxy groups in the same protein. The free carboxy group preferably is a carboxy terminal or a carboxy group of a diacidic alpha amino acid.

The compounds carrying a $H_2NNH—$ group, a thiol-reactive group, an activated carboxy group, or an amino group may be bifunctional coupling reagents or an antibody or a superantigen. The groups are bound directly to saturated carbon atoms except for the $H_2NNH—$ group that as an alternative also may be bound to a karbonyl carbon. The groups may have been introduced onto the the antibody or superantigen by common derivatization.

Recombinant techniques provide efficient means for the manufacture of conjugates in which the parts are specifically linked together from a terminal carboxy group in one moiety to a terminal amino group in the other moiety. A linkage structure consistent with the technique applied may be inserted.

The reagents employed are selected so that they will provide the linkage —B— as defined above. Common bifunctional reagents have the formula Z—B'—Z' where Z and Z' are are functional groups that are mutually consistent with each other and allowing for covalent coupling at a functional group present on a protein. See above. B' is an inert bridge that may contain the same structures as given for the linkage —B— above. Particularly Z and Z' may be identical or different and selected among a thiol group, a thiol-reactive group, an activated carboxy, $—CONHNH_2$ etc. For a definition of these groups se below under the heading Novel Reagents.

The method we have used for the conjugates employed in the experimental part comprises the steps of:

(i) reacting the antibody or the superantigen with an organic reagent containing a thiol-reactive group and an amino-reactive group to the formation of an antibody or a superantigen carrying the thiol-reactive group, and (ii) reacting the remaining part of the superantigen and the antibody with an organic reagent containing a thiol group or a protected thiol group and an amino-reactive group to the formation of a superantigen or an antibody carrying the thiol group or the protected thiol group, whereupon (iii) the obtained products from steps (i) and (ii), respectively, are reacted with each other to the formation of a conjugate in which the superantigen is linked to the antibody via a disulfide or thioether.

The coupling conditions for each group are known per see as applied to protein chemistry. The coupling may proceed stepwise or in one step by creating intermediary functional groups that may be linked to the starting material by inert spacer arms. In general the conditions under which the synthesis and purification/recovering of the conjugate take place are always non-denaturing for the proteins involved. This normally means aqueous media and a pH-value and temperature within in the ranges pH 3–10 and 0°–50° C., respectively. The exact values depend on the groups to be reacted and the conjugate to be recovered. See more under the heading Novel reagents.

Novel Reagents (Developed in Connection with the Invention).

For the chemical synthesis of conjugates having the linkage —B—, we have developed a novel heterobifunctional reagent that complies with the general formula II:

$$Z_1RCONHCH_2CH_2(OCH_2CH_2)_nO(CH_2)_mZ_1' \qquad (II)$$

m and n have the same meaning as above for formula (I). $Z_1$ is an HS-reactive electrophilic group, thiol (—SH) or protected thiol (e.g. AcS—), with the provision that a thiol group and a hydroxy group must not be bound to one and the same carbon atom in R. Examples of HS-reactive electrophilic groups are:

(i) halogen that is bound to a saturated carbon atom, preferably in the form of an alfa-halo-alkylcarbonyl (e.g. $Z_1CH_2CO—$);

(ii) activated thiol, preferably a so called reactive disulfide ($—SSR_1$) that is bound to a saturated carbon atom;

(iii) 3,5-dioxo-1-aza-cyclopent-3-en-1-yl.

For a definition of reactive disulfide see e.g. EP-A-128,885 which is incorporated by reference.

$Z_1'$ is an activated carboxy, i.e. an electrophilic group. Examples are carboxylic acid halides (—COCl, —COBr, and —COI), mixed carboxylic acid anhydrides ($—COOOCR_1$), reactive esters, such as N-succinimidyloxycarbonyl, $—C(=NH)—OR_2$, 4-nitrophenylcarboxylate ($—CO—OC_6H_4NO_2$) etc. $R_1$ and $R_2$ may be lower alkyl ($C_1$–$C_6$) and $R_2$ also benzyl.

One of the advantages of our novel reagents are that they result in uniform conjugate substances with regard to the integer n in the structure $(OCH_2CH_2)_n$, i.e. n is the same for each individual molecule of a given conjugate substance.

Functional groups reacting with $Z_1'$ and $Z_1$ may be present on native antibody active molecules or native superantigens or can be introduced on them. The $Z_1'$ and $Z_1$ terminals can then be reacted selectively with the appropriate antibody or superantigen in a manner known per se for these types of groups.

Known techniques encompass chain elongation either starting from our novel reagent or from the compounds to be conjugated.

Chain elongation utilizing our novel reagent may e.g. result in conjugates in which —B— is:

(1) $—COR'—S_r—RCONHCH_2CH_2(OCH_2CH_2)_nO(CH_2)_mCOY—$; $\underline{C}O$ binds to NH, (2) $—COR'—S_r—RCONHCH_2CH_2(OCH_2CH_2)_nO(CH_2)_mCONHNH—R''NH\underline{N=}—$; $\underline{N=}$ is usually bound to a $sp^2$-hybridized carbon derived from an oxidized carbohydrate structure in an antibody or a superantigen (when being a glycoprotein), (3) $—\underline{C}O(CH_2)_mO(CH_2CH_2)_nCH_2CH_2NHCOR'—S_r—$(cont.) (cont.)$—RCONHCH_2CH_2(OCH_2CH_2)_nO(CH_2)_mCOY—$; $\underline{C}O—$ is bound NH, (4) $—CO(CH_2)_mO(CH_2CH_2O)_nCH_2CH_2NHCOR'—S_r—$ (cont.) (cont.)$—RCONHCH_2CH_2(OCH_2CH_2)_nO(CH_2)_mCONHNH—R''NH\underline{N=}$; $\underline{N=}$ is bound as above in (2), R, R' and R" are alkylene selected in the same way as R in formula (I). r has the same meaning as above.

The reagent (Formula II) can be prepared starting from compounds complying with formula III:

$$NH_2CH_2CH_2(OCH_2CH_2)_nO(CH_2)_mCOOH \qquad (III)$$

m equals an integer 1 or 2. n equals an integer 1–20, such as 2–20 or 3–9.

The synthesis of certain compounds complying with formula III with m=1 and 2, and n=1–10 have been described before (Jullien et al, Tetrahedron Letters 29(1988) 3803–06; Houghton and Southby, Synth.Commun. 19(18) (1989)3199–3209; and EP-A-410,280 (publ. 20.1.91) and Slama and Rando, Carbohydrate Research 88(1981) 213–221 and Biochemistry 19(1980)4595–4600).

Novel reagents complying with formula II can be synthesized by reacting a compound of formula III with a bifunctional reagent of formula Z—B'—Z' known per se, where $Z=Z_1$, B'=R" that is as previously defined for R and R', and Z'=activated carboxy as defined above. After the reaction the —COOH function is transformed to an activated carboxy group, e.g. $Z_1'$=activated ester, such as N-succinimidyloxycarbonyl, 4-nitrophenyloxycarbonyl, 2,4-dinitrophenyloxykarbonyl etc.

The novel compounds of formula (III) and their novel derivatives comply with polyethers having the general formula:

$$XCH_2CH_2(OCH_2CH_2—)_nOCH_2Y \qquad (IV)$$

n is an integer 2–20, preferably 3–20 or 3–9. X is $H_2N—$ including the protonated form thereof ($^+H_3N—$) or substituted $H_2N—$ that is transformable to $H_2N—$, preferably by hydrolysis or reduction. Examples are unsubstituted amino ($H_2N—$); nitro; amido (carbamido), such as lower acylamido (formylamido, acetylamido . . . hexanoylamido)

including acylamido groups that have electron-withdrawing substituents on the alpha carbon atom of the acyl moiety and then particularly $CF_3CONH$—, $CH_3COCH_2CONH$— etc; phtalimidoyl which possibly is ring substituted; carbamato (particularly $R_1$'OCONH— and ($R_1$'OCO)($R_2$'OCO)N—, such as N-(t-butyloxycarbonyl)amino (Boc), N-(benzyloxycarbonyl)amino and di(N-(benzyloxycarbonyl))amino (Z and diZ, respectively) which possibly are ring substituted; alkyl amino in which the carbon atom binding to the nitrogen atom is alpha to an aromatic system, such as N-monobenzylamino and dibenzylamino, N-tritylamino (triphenylmethylamino) etc including analogous groups where the methyl carbon atom (including benzylic carbon atom) atom is replaced with a silicon atom (Si), such as N,N-di(tert-butylsilyl)amino; and 4-oxo-1,3,5-triazin-1-yl including such ones that are substituted with lower alkyl in their 3- and/or 5-positions.

Above and henceforth $R_1$' and $R_2$' stand for lower alkyl, particularly secondary and tertiary alkyl groups, and a methyl group that is substituted with 1–3 phenyl groups that possibly are ring substituted. Lower alkyl and lower acyl groups have 1–6 carbon atoms.

Y is carboxy (—COOH including —$COO^-$) or a group that is transformable to carboxy, preferably by hydrolysis or oxidation. The most important groups are the ester groups in which the carbonyl carbon atom or the corresponding atom in orto esters binds to the methylene group in the right terminal of formula (I). Examples are alkyl ester groups (—$COOR_1$'); ortho ester groups (—$C(OR_3')_3$) and reactive ester groups as defined above. $R_3$' has the same meaning as previously defined for $R_1$, Other groups Y are —CHO, —CN, —$CONH_2$, —$CONR_1$'$R_2$$^{1}$' where $R_1$' and $R_2$' have the same meaning as previously.

The compound of formula IV may be synthesized from known starting materials by combining methods that are known per se. Appropriate synthetic routes are:

A. Formation of the chain.

B. Transformation of terminal functional groups.

C. Transformation of a symmetric polyether to an unsymmetric ether.

D. Splitting of a bisymmetric chain into two identical fragments.

Convenient starting materials that have the repeating unit —$OCH_2CH_2$— are commercially available. Examples are oligoethylene glycols having 2 to 6 repeating units. other suitable compounds with identical terminal groups are corresponding dicarboxylic acids and diamines. Convenient starting materials that have different terminal groups are omega-hydroxy monocarboxylic acids in which the terminal groups are spaced apart by a pure polyethtleneoxide bridge. Such compounds having up to 5 repeating units have been described in the prior art (Nakatsuji, Kawamura and Okahara, Synthesis (1981) p.42).

Pharmaceutical Compositions and their Manufacture

The pharmaceutical composition of the invention comprises formulations that as such are known within the field but now containing our novel conjugate. Thus the compositions may be in the form of a lyophilized particulate material, a sterile or aseptically produced solution, a tablet, an ampoule etc. Vehicles, such as water (preferably buffered to a physiologically pH-value such as PBS) or other inert solid or liquid material may be present. In general terms the compositions are prepared by the conjugate being mixed with, dissolved in bound to or otherwise combined with one or more water-insoluble or water-soluble aqueous or non-aqueous vehicles, if necessary together with suitable additives and adjuvants. It is imperative that the vehicles and conditions shall not adversely affect the activity of the conjugate. Water as such is comprised within the expression vehicles.

Administration and Methods of Use.

Normally the conjugates will be sold and administered in predispensed dosages, each one containing an effective amount of the conjugate that, based on the result now presented, is believed to be within the range 10/ug–50 mg. The exact dosage varies from case to case and depend on patient's weight and age, administration route, type of disease, antibody, superantigen, linkage (—B—) etc.

The administration route is as commonly known within the field, i.e. a target cell lysing effective amount or a therapeutically effective amount of a conjugate according to the invention is contacted with the target cells. For the indications specified above this mostly means parenteral administration, such as injection or infusion (subcutanously, intravenously, intra-arterial, intramuscularly) to a mammal, such as a human being. The conjugate may be administered locally or systemically to the individual to be treated.

By "target cell lysing effective amount" is contemplated that the amount is effective in activating and directing CTLS to destroy the target cell.

The invention is defined in the appended claims that are part of the description. The invention will now be illustrated by a number of embodiments that in no way limit the general concept we have discovered. The experimental part presents in Part I the chemical synthesis of conjugates and in Part II effects of the conjugates prepared in example 4 on the activation of T-Cells for lysing target cells.

EXPERIMENTAL PORTION PART 1

PREPARATION OF omega-AMINO-PEG-KARBOXYLIC ACID

Isopropyl 8-hydroxy-3,6-dioxa-octanoate (1).

Sodium (23 g, 1.0 mole) in form of chips was added in portions to diethylene glycol (500 ml) under nitrogen atmosphere. When the sodium had reacted completely, the mixture was cooled to room temperature and bromoacetic acid was added (76 g, 0.5 mole) under stirring. After 18 hours at 100° C. the excess of diethylene glycol was distilled off at about 4 mm Hg. Thereafter isopropyl alcohol (400 ml) and in portions acetyl chloride (51 g, 0.65 mole) were added. After stirring for 18 hours at 65° C. the mixture was cooled to room temperature and neutralized with sodium acetate (3.5 g, 0.15 mole). The mixture was filtered and the filtrate evaporated nearly to dryness, whereupon it was dissolved in water (200 ml). The water phase was extracted with 1,1,1-trichloro-ethane (3×50 ml). The pooled organic phases were washed with water (20 ml). The product was extracted from the pooled water phases with dichloromethane (50 ml) that after evaporation gave an oil (55 g).

Isopropyl 11-hydroxy-3,6,9-trioxa-undecanoate (2).

Sodium (23 g, 1.0 mole) in form of chips was added in portions to triethylene glycol (700 ml) under nitrogen atmosphere. When the sodium had reacted completely, the mixture was cooled to room temperature and bromoacetic acid was added (76 g, 0.5 mole) under stirring. After 18 hours at 100° C. the excess of diethylene glycol was distilled off at about 4 mm Hg. Thereafter isopropyl alcohol (400 ml) and in portions acetyl chloride (51 g, 0.65 mole) were added. After stirring for 18 hours at 65° C. the mixture was cooled to room temperature and neutralized with sodium acetate (3.5 g, 0.15 mole). The mixture was filtered and the filtrate evaporated nearly to dryness, whereupon it was dissolved in water (200 ml). The water phase was extracted with 1,1,1- trichloro-ethane (3×50 ml). The pooled organic phases were washed with water (20 ml). The product was extracted from the pooled water phases with dichloromethane (50 ml) that after evaporation gave an oil.

$^1$H-n.m.r.($CDCl_3$); 1.26(d,6H);3.07(s,2H);3.6–3.8(m, 12H); 4.11(s,2H);5.09(m,1H).

8-(N-phtalimidoyl)-3,6-dioxa-octanol (3).

8-Chloro-3,6-dioxa-octanol (365 g, 2.2 mole, prepared from from triethylene glycol and $SOC_2$) was dissolved in dimethyl formamide (400 ml) and potassium phtalimide (370 g, 2.0 mole) was added under stirring. After stirring for 18 hours at 110° C. dimethyl formamide was distilled off at reduced pressure. The residue was suspended in toluene (1.5 1) at 40–50° C. and potassium chloride was filtrated off. The product crystallizes at cooling (−10° C.). A second fraction is available from the mother liquor by concentrating it and repeating the crystallization procedure.

$^1$H-n.m.r.($CDCl_3$); 2.90(s,1H);3.51–3.58(m,2H) ;3.60–3.68(m,6H);3.73–3.78(t,2H);3.89–3.94(t,2H) ;7.70–7.89(m,4H).

Isopropyl 17-(N-phtalimidoyl)-3,6,9,12,15-pentaoxaheptadecanoate (4).

A solution of pyridine (2.8 ml, 35 mmole) in dichloromethane (30 ml) was added dropwise under stirring at about −5° C. to a solution of 8-(N-phtalimidoyl)-3,6-dioxa-octanol (3) (8.5 g, 36 mmole) and trifluoromethanesulfonic acid anhydride (10.2 g, 36 mmole) in dichloromethane. After about 30 minutes the organic phase was washed with 0.5 M hydrochloric acid and water. After drying ($Na_2SO_4$) and filtration isopropyl 8-hydroxy-3,6-dioxa-octanoate (1) (12 g, 48 mmole) and $Na_2PO_4$ (6.5, 46 mmole) were added, and the mixture was vigorously stirred for 20 hours at room temperature. The reaction mixture was filtrated and the filtrate evaporated. The residue was partitioned between 1,1,1-trichloroethane and water. Evaporation of the organic phase resulted in an oil (13 g).

$^1$H-n.m.r.($CDCl_3$); δ 1.26(d,6H);3.58–3.76(m,18H);3.90 (t,2H); 4.11(s,2H);5.09(m,1H);7.70–7.89(m,4H).

17-(N-phtalimidoyl)-3,6,9,12,15-pentaoxa-heptadecanoic acid (5).

Isopropyl 17-(N-phtalimidoyl)-3,6,9,12,15-pentaoxa-heptadecanoate (4) (13 g) was dissolved in tetrahydrofuran (50 ml) and hydrochloric acid (conc., 50 ml)). After 16 hours at room temperature the solution was diluted with water (200 ml) and tetrahydrofuran was removed at reduced pressure. The water phase was washed with toluene (1×) and extracted with dichloromethane (2×). Drying ($Na_2SO_4$) and evaporation of the organic phase resulted in the product in form of an oil (8.5 g)

$^1$H-n.m.r.($CDCl_3$): δ 3.57–3.76 (m,18H);3.91(t,2H);4.11 (s,2H); 4.8(br,2H);7.65–7.90(m,4H).

Isopropyl 17-amino-3,6,9,12,15-pentaoxa-heptadecanoate (6)

17-(N-phtalimidoyl)-3,6,9,12,15-pentaoxa-heptadecanoic acid (5) (8.5 g) was dissolved in 150 ml ethanol and 3 ml hydrazine hydrate. The solution was stirred at room temperature for 16 hours, whereupon HCl (100 ml, 3M) was added and the solution was then refluxed for 3 hours. After cooling to room temperature and filtration, pH was adjusted (pH 9, NaOH) and the filtrate was evaporated almost to dryness. Water was added and re-evaporation almost to dryness was carried out, whereupon the pH of the solution was adjusted (pH 4, HCl) followed by evaporation to dryness. The product was treated with isopropanol (100 ml) and acetyl chloride (2 ml) at room temperature during the night and evaporated. The residue was collected in water and extracted into dichloromethane at an alkaline pH (7–11). Evaporation resulted in the product (3.3 g).

$^1$H-n.m.r.($CH_3OD$): δ 1.26(d,6H);3.17(t,2H);3.65–3.80 (m,l8H); 4.16(s,2H);5.07(m,1H).

FORMULAE OF SYNTHESIZED AMINO-PEG-CARBOXYLIC ACIDS $H\text{-}(OCH_2CH_2)_nCH_2CO—OCH(CH_3)_2$ Compound 1: n=1

Compound 2: n=1

$PhtN—CH_2CH_2—(OCH_2CH_2)_2OH$

Compound 3, PhtN—=N-phtalimidoyl $PhtN\text{-}CH_2CH_2—(OCH_2CH_2)_4CH_2CO—OCH(CH_3)$
2

Compound 4, PhtN—=N-phtalimidoyl $PhtN\text{-}CH_2CH_2—(OCH_2CH_2)_4CH_2CO—OH$

Compound 5

$H_2N—CH_2CH_2—(OCH_2CH_2)_4CH_2CO—OH$

Compound 6

PREPARATION OF BIFUNCTIONAL REAGENTS AND COUPLING PRODUCTS

Structural formulae are set forth on a separate page.

EXAMPLE 1

Preparation of N-hydroxysuccinimide ester of 17-iodoacetylamino-3,6,9,12,15 pentaoxaheptadecanoic acid A. Preparation of 17-iodoacetylamino -3,6,9,12,15-pentaoxaheptadecanoic acid (A)

Isopropyl 17-amino-3,6,9,12,15-pentaoxaheptadecanoate (see part I of the experimental part) (1.1 g, 3.2 mmole) was dissolved in 3 ml of 1 M sodium hydroxide solution and left at room temperature for 30 min. 1.5 ml of 6 M hydrochloric acid was added and the mixture was evaporated to dryness. The residue was taken up in dichloromethane and filtered to give 545 mg of 17-amino-3,6,9, 12,15-pentaoxaheptadecanoic acid after evaporation of the solvent. 460 mg (1,39 mmoles) of this compound were dissolved in 10 ml of borate buffer pH 8.4. The solution was deaerated with nitrogen gas. A solution of 432 mg (1.52 mmoles) of N-succinimidyl 2-iodoacetate in 5 ml of dioxane was added dropwise during 1 min pH was kept at 8.4 by addition of 5 M NaOH. The reaction solution was stirred for 15 min during inlet of nitrogen gas. According to thin layer chromatography (eluent: $CH_2Cl_2$-MeOH 60:35) the reaction was completed in some few minutes. After 15 min the pH of the reaction solution was adjusted to 3 and the solution was frozen and lyophilized. The reaction mixture was fractionated on a reversed phase column PEP-RPC HR 30/26 (Pharmacia Biosystems AB) using a gradient of 0–13% acetonitrile with 0.1% trifluoroacetic acid followed by isocratic separation at 13% acetonitrile, 0.1% TFA. Fractions from the desired peak were pooled and lyophilized giving 351 mg of 17-iodoacetylamino-3,6,9,12,15-pentaoxaheptadecanoic acid (A). Yield: 76%.

The structure of the product was established by the aid of its NMR spectrum. $^1H$ NMR spectrum ($D_2O$) expressed as δ-values:

$IC\underline{H}_2C$ 4.23 s, $OC\underline{H}_2COH$ 3.76 s $$-OC\underline{H}_2C\underline{H}_2O- \ 3.71\text{–}3.76, \quad -NHCH_2C\underline{H}_2O- \ 3.65\ t,$$
$$-NHC\underline{H}_2CH_2O- \ 3.41$$

B. Preparation of N-hydroxysuccinimide ester of 17-iodoacetylamino-3,6,9,12,15-pentaoxaheptadecanoic acid (B)

Hydroxysuccinimide (4.5 mg, 39 μmole) was weighed in the reaction vial. 17-Iodoacetylamino-3,6,9,12,15-pentaoxaheptadecanoic acid (A) (18.3 mg, 39 μmole) was dissolved in 0.55 ml dried dioxane and added to the reaction vial. The vial was deareated with nitrogen gas and then a solution of 8.0 mg (39 μmole) dicyclohexylcarbodiimide in 0.15 ml of dried dioxane was added dropwise to the reaction vial. The vial was filled with nitrogen gas, closed and placed in the dark. The reaction solution was stirred for 3.5 h. The precipitate formed was removed by filtration. The percentage formed product B in the filtrate was determined by NMR-analysis to be 89%.

EXAMPLE 2

Preparation of (17-iodoacetylanino-3,6,9,12,15-pentaoxaheptadecanoylamino)-immunoglobulin (C)

A. Monoclonal Antibody Mab C215

A monoclonal antibody of immunoglobulin class IgG2a (Mab C215) (34 mg, 0.218 μmole) dissolved in 17.7 ml of 0.1 M borate buffer pH 8.1 containing 0.9% sodium chloride was added to a reaction vial. 146 μl of a dioxane solution containing 3.6 mg (6.4 mole) of N-hydroxysuccinimide ester of 17-iodoacetylamino-3,6,9,12,15-pentaoxaheptadecanoic acid (B) was injected into the buffer solution and the reaction was completed during stirring for 25 min. at room temperature. The reaction vial was covered with folie to exclude light. Excess of reagent B was removed by fractionation on a Sephadex G 25 K 26/40 column using 0.1 M phosphate buffer pH 7.5 containing 0.9% sodium chloride as eluent. Fractions containing the desired product C were pooled. The solution (22 ml) was concentrated in an Amicon cell through a YM 30 filter to 8 ml. The concentration and degree of substitution were determined with amino acid analysis to be 4.7 mg/ml and 18 spacer per Mab C215 respectively.

B. Monoclonal Antibody Mab C242

A monoclonal antibody (Mab C242) of the immunoglobulin class IgG 1 was reacted with 15, 20 and 22 times molar excess of N-hydroxysuccinimide ester of 17-iodoacetylamino-3,6,9,12,15-pentaoxaheptadecanoic acid (B) respectively according to the procedure described in example 2.A giving nona, dodeca and 35 tetradeca(17-iodoacetylamino)-3,6,9,12,15-pentaoxaheptadecanoylamino)-Mab C242. (C)

C. Monoclonal Antibody Mab C

A monoclonal antibody (Mab C) of the immunoglobulin class IgG 2a was reacted with 14 and 18 times molar excess of N-hydroxysuccinimide ester of 17-iodoacetylamino-3,6,9,12,15-pentaoxaheptadecanoic acid (B) respectively according to the procedure described in example 2A giving tetra and hepta(17-iodoacetylamino-3,6,9,12,15-pentaoxaheptadecanoylamino)-Mab C. (C)

EXAMPLE 3

Preparation of 2-mercaptopropionylamino-$Eu^3$-labelled-staphylococcal enterotoxin A (SEA)

A. Preparation of $Eu^{3+}$ labelled SEA (D)

SEA (freezed dried product from Toxin Technology Inc.) (2 mg, 72 μnmole) was dissolved in 722 μl milli-Q water and added to a 15 ml polypropylene tube. 100 μl of 0.1 M borate buffer pH 8.6 was added and then 2160 nmoles of $Eu^{3+}$-chelate reagents (Pharmacia Wallac Oy) in 178 μl of milli-Q. The reaction was completed at room temperature over night. Excess reagent was removed by fractionation of the reaction solution on a Sephadex G 25 PD 10 column (Pharmacia Biosystems AB) using 0.1 M phosphate buffer pH 8.0 as eluent. Fractions with the desired product D were pooled. The solution (3 ml) was concentrated in an Amicon cell through an YM5 filter to a volume of 0.8 ml. The concentration was determined with amino acid analysis to be 1.7 mg/ml. The degree of substitution was determined by comparing with a $EuCl_3$ standard solution to be 0.8 $Eu^{3+}$ per SEA.

B1. Preparation of 3-(2-pyridyldithio)propionylamino $Eu^{3+}$ labelled SEA (E) and 3-mercaptopropionylamino $Eu^{3+}$ labelled SEA (F)

$Eu^{3+}$-SEA (1.24 mg, 44.8 μnmoles) in 0.75 ml of 0.1 M phosphate buffer pH 8.0 was added to a 15 ml polypropylene tube. 35 μl (180 nmole) of a solution of 1.6 mg of N-succinimidyl 3-(2-pyridyldithio)-propionate in 1 ml of ethanol was added to the tube and the reaction solution was stirred for 30 min at room temperature. The obtained product E was not isolated before being reduced to product F.

To the reaction solution from above were added 20 μl of 0.2 M $Eu^{3+}$-citrate solution and 50 μl of 2 M acetic acid to adjust the pH to 5. Thereafter a solution of 3.1 mg of dithiotreitol (Merck) in 0.1 ml of 0.9% sodium chloride was added and the reaction solution was stirred for 20 min at room temperature. Thereafter the total volume was adjusted to 1 ml by addition of 50 pl of 0.9% sodium chloride solution. The reaction solution (1 ml) was placed on a Sephadex G25 NAP-10 column (Pharmacia Biosystems AB) and desired product F was eluted by addition of 1.5 ml of 0.1 M phosphate buffer pH 7.5 containing 0.9% sodium chloride. The eluted product F was collected in a 15 ml polypropylene tube and immediately used in the synthesis of product G to avoid reoxidation to a disulfide compound.

B2. Preparation of 2-mercaptopropionylaminostaphylococcal enterotoxin A (SEA) (F2)

Native SEA (freeze dried product from Toxin Technology Inc) or recombinant prepared SEA (rSEA) was reacted with 2 times molar excess of N-succinimidyl 3-(2-pyridyldithio)-propionate according to the procedure described in example 3B1.

The degree of substitution was determined with UV-analysis according to Carlsson et al (Biochem. J. 173 (1978)723–737) to be 1.9 mercaptopropionyl group per SEA.

EXAMPLE 4

Preparation of the SEA-monoclonal Antibody Conjugate (G1 och G2)

A. Conjugates Between $Eu^{3+}$-SEA and Mab C215 (G1)

To the solution of 4-mercaptopropionylamino $Eu^{3+}$ labelled SEA (F) described in example 3B was added 1.2 ml of a solution of octadeca(17-iodoactylamino-3,6,9,12,15-pentaoxaheptadecanoylamino)Mab C215 (C) (4 mg) in 0.1 M phosphate buffer pH 7.5 containing 0.9% sodium chloride. The reaction was completed by standing at room temperature over night. Unreacted iodinealkyl groups were then blocked by addition of 5 μl (1.2 μmole) of a solution of 20 μl mercaptoethanol in 1 ml of water. The reaction solution was left for 4 h at room temperature and then filtrated. The filtrate was then fractionated on a Superose 12 HR 16/50 column (Pharmacia Biosystems AB) using as eluent 0.002 M phosphate buffer pH 7.5 containing 0.9% sodium chloride. Fractions with the desired product G were pooled and analysed. The protein content was 0.22 mg/ml determined by amino acid analysis. The degree of substitution was one SEA per IgG determined by $Eu^{3+}$ determination. The product was also studied for immunostimulating properties and antibody binding capacity.

By increasing the amount of compound (F) in relation to compound (C) higher degree of substitution was obtained.

B. Conjugates Between rSEA and Mab C215 (G2)

Octadeca (17-iodoacetylamino-3,6,9,12,15-pentaoxaheptadecanoylamino)Mab C215 (C) was reacted with 1.8 times molar excess of 2-mercaptopropionylamino-rSEA (F2) according to the procedure described in example 4A. The composition of the conjugate was analysed by sodium dodecylsulfate polyacrylamide gel electrophoresis (SDS-PAGE) on Phast-Gel™ gradient 4-15 and the bonds were scanned with Phast IMAGE (Pharmacia Biosystems AB). The conjugate obtained was composed of 6% Mab C215 with three SEA, 15% with two SEA, 28% with one SEA and 51% unsubstituted Mab C215.

In another experiment 2.7 times molar excess of F2 was used giving a conjugate with the composition 15% Mab C215 with three SEA, 25% with two SEA, 34% with one SEA and 26% of unsubstituted Mab C215.

C. Conjugates Between rSEA and Mab C242

C1. Tetradeca(17-iodoacetylamino-3, 6,9,12,15-pentaoxaheptadecanoylamino)Mab C242 (C) was reacted with 3.2 times molar excess of 2-mercaptopropionylamino-rSEA (F2) according to the procedure described in example 4A. The composition of the conjugate was analysed as described in example 4 B and was found to be 4% Mab C242 with four SEA, 12% with three SEA, 28% with two SEA, 36% with one SEA and 20% of unsubstituted Mab C242.

The same reaction was run but the reaction product was treated 4 h with 0.2 M hydroxylamine before column fractionation to remove unstable bonds between Mab C242 and the spacer and between SEA and the mercaptopropionyl group. The conjugate formed had the composition 1% Mab C242 with four SEA, 12% with three SEA, 27% with two SEA, 36% with one SEA and 24% of unsubstituted Mab.

C2. Dodeca(17-iodoacetylamino-3,6,9,12,15-pentaoxaheptadecanoylamino)Mab C242 (C) was reacted with 3 times molar excess of 2-mercaptopropionylamino-rSEA (F2) according to the-procedure described in example 4A. The conjugate obtained had the composition 6% Mab C242 with three SEA, 26% with two SEA, 36% with one SEA and 31% unsubstituted Mab C242.

C3. Nona(17-iodoacetylamino-3,6,9,12,15-pentaoxaheptadecanoylamino)Mab C242 (C) was reacted with 3 times molar excess of 2-mercaptopropionylamino-rSEA (F2) according to the procedure described in example 4A. The conjugate obtained had the composition 13% Mab C242 with two SEA, 39% with one SEA and 46% unsubstituted Mab C242.

D. Conjugates Between rSEA and Mab C

D1. Hepta(17-iodoacetylamino-3,6,9,12,15-pentaoxaheptadecanoylamino)Mab C was reacted with 5.4 times molar excess of 2-mercaptopropionylamino-rSEA (F2) according to the procedure described in example 4A. The composition of the conjugate was analysed as described in example 4B and was found to be 15% with four SEA, 24% with three SEA, 29% with two SEA, 19% with one SEA, 3% unsubstituted Mab C and 10% in a dimeric form.

The same reaction was run with 0.2 M hydroxylamine present to remove unstable bonds between Mab C and spacer and between SEA and the mercaptopropionyl group. The conjugate formed had the following composition 11% Mab C with three SEA, 24% with two SEA, 30% with one SEA, 18% of unsubstituted Mab C and 17% in a dimeric form.

D2. Tetra(17-iodoacetylamino)-3,6,9,12,15-pentaoxaheptadecanoylamino)Mab C was reacted with 5.7 times molar excess of 2-mercaptopropionylamino-rSEA (F2) according to the procedure described in example 4B. The conjugate had the following compositon 8% Mab C2 with four SEA, 18% with three SEA, 30% with two SEA, 26% with one SEA, 5% of unsubstituted Mab C and 12% in a dimeric form.

EXAMPLE 5

Preparation of [17-(3-mercaptopropionylamino)-3,6,9,12,15-pentaoxaheptadecanoylamino]-rSEA (I)

A. Preparation of [17-(3-(2-pyridyldithio)propionylamino]-3,6,9,12,15-pentaoxaheptadecanoylamino)-rSEA (H)

A solution of N-hydroxysuccinimide ester of 17-[3-(2-pyridyldithio)propionylamino]-3,6,9,12,15-pentaoxaheptadecanoic acid (K) (0.53 mg (896 nmoles) in 43 $\mu$l of dioxane) was injected into a solution of 3.67 mg (128 nmoles) of rSEA in 1 ml of 0.1 M phosphate buffer pH 7.5 containing 0.9% of sodium chloride. The reaction was completed in 30 min at room temperature. 100 $\mu$l was taken for analysation of degree of substitution. The rest was stored frozen until it was reduced to product I.

The degree of substitution was determined by desalting 100 $\mu$l of the reaction solution on a Sephadex G50 NICK column (Pharmacia Biosystems AB) and analysing the eluate with UV-spectroscopy according to Carlsson et al (Biochem. J. 173(1978)723–737). 2.7 spacers were coupled to rSEA.

B. Preparation of [17-(3-mercaptopropionylamino)-3,6,9,12,15-pentaoxaheptadecanoylamino]-rSEA (I)

The pH of the reaction solution with product H (0,9 ml) was adjusted with 2 HCl to pH 4.4 and 2.9 mg of dithiotreitol dissolved in 75 $\mu$l sodium chloride was added. The reduction was completed in 30 min. The reaction solution was added to a Sephadex G25 NAP 10 column (Pharmacia Biosystems AB) and eluted with 1.5 ml of 0.1 M phosphate buffer pH 7.5 with 0.9% NaCl and immediately used in the synthesis of product J in example 11.

EXAMPLE 6

Preparation of SEA-monoclonal Antibody Conjugate J with Double Spacer

Dodeca(17-iodoacetylamino-3,6,9,12,15-pentaoxaheptadecanoylamino)Mab C242 (C) (4.2 mg, 27 nmoles in 1.0 ml of 0.1 M phosphate buffer pH 7.5 with 0.9% NaCl) was reacted during 43 h with [17-(3-mercaptopropionylamino)-3,6,9,12,15-pentaoxaheptadecanoylamino]-rSEA (I) (1.17 mg, 42 nmoles in 1 ml of the above buffer) in the dark in nitrogen atmosphere. Thereafter 1.14 $\mu$mole of mercaptoethanol was added. After another 1 h the reaction solution was fractionated on a Superdex 200 HR 16/65 column. The product was eluated with 2 mM phosphate buffer pH 7.5 with 0.9% NaCl. Fractions with the desired product J were pooled and analysed as described in example 4B. The conjugate was composed of 9% Mab C242 with two SEA, 25% with one SEA and 66% of unsubstituted Mab C242.

A

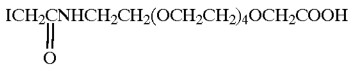

B

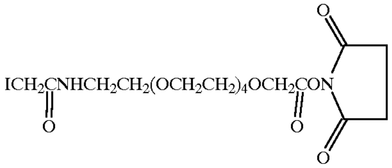

C

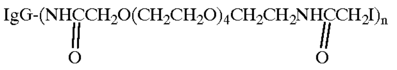

n = 4, 7, 9, 12, 14, 18

D

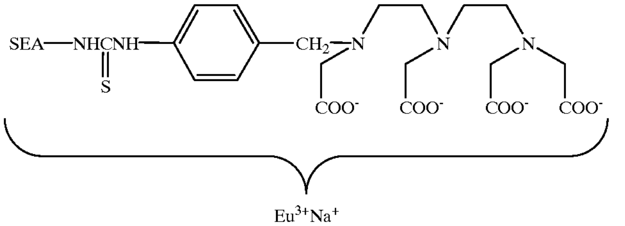

(Eu$^{3+}$—SEA)

E

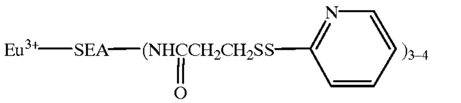

F1

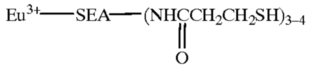

F2

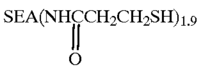

G1

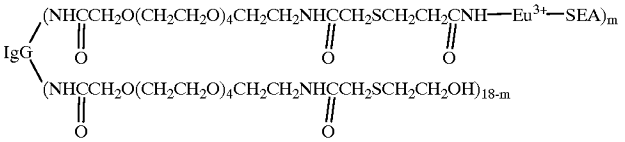

G2

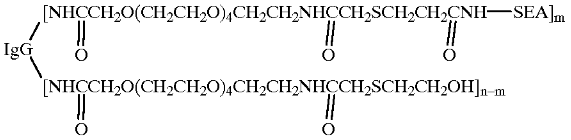

H

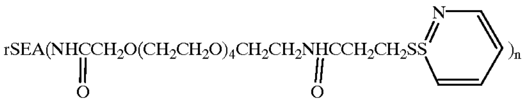

I

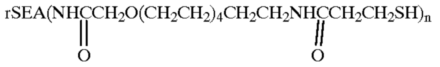

J

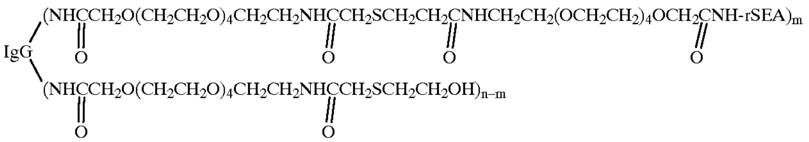

EXPERIMENTAL PART II

Effects of Superantigen-antibody Conjugates on Cells

The bacterial toxin used in the following experiments was Staphylococcus enterotoxin A (SEA) obtained from Toxin Technologies (Wisconsin; USA) or produced as a recombinant protein from *E. Coli.*

The antibodies were C215, C242 and Thy-1.2 mAbs. C215 is an 1gG2a mAb raised against human colon carcinoma cell line and reacts with a 37 kD protein antigen on several human colon cell lines. References to these mAbs have been given above. The conjugates were prepared as described in the preceding part.

Before the priority date studies had only been performed with Eu$^{3+}$ labelled SEA-C215 mAb conjugates. During the priority year the results have been verified with unlabelled SEA-215, SEA-242 and SEA-Thy-1.2 mAb conjugates. The results now incorporated refer to unlabelled conjugates.

To determine the cytotoxicity mediated by the SEA-C215 mAb conjugate and unconjugated SEA and C215 mAb against colon carcinoma cells lacking MHC Class II or expressing low but undetectable amounts of MHC Class II, we employed various human SEA expanded T cell lines as effector cells and a panel of colon carcinoma cells and MHC Class II$^+$ Raji cells as target cells. The colon carcinoma cell lines Colo205, SW620 and WiDr, all lacked expression of MHC Class II, as determined by staining with mAbs against HLA-DR, HLA-DP and HLA-DQ and FACS analysis. The SEA expanded T cell lines were established from peripheral blood by weekly restimulations with mitomycin C treated MHC Class II BSM lymphoma cells precoated with SEA in the presence of recombinant IL-2 (20 units/ml). These T cell lines were strongly cytotoxic towards Raji or BSM cells coated with SEA but not to uncoated cells or cells coated with staphylococcal enterotoxin B (SEB). This SEA induced killing is dependent on interaction of SEA with MHC Class II on the target cell as determined by the use of blocking HLA-DR antibodies, MHC Class II$^-$ Raji mutant cells and HLA-DR transfected L-cells (Dohlsten et al., Immunology 71 (1990) 96–100. These T cell lines could be activated to kill C215$^+$ MHC Class II$^-$ colon carcinoma cells by the C215-SEA conjugate. In contrast unconjugated SEA and C215 mAb were unable to induce more than marginal T cell killing against the C215$^+$ MHC Class II$^-$ colon carcinoma cells. The staphylococcal enterotoxin antibody conjugate dependent cell-mediated cytotoxicity was dependent on binding of the SEA-C215 mAb conjugate to the C215$^+$ tumor cells. The specificity in this binding was demonstrated by the fact that excess of unconjugated C215 mAb but not the irrelevant C242 and w6/32 mAbs inhibited the lysis of the colon carcinoma cells. CD4$^+$ and CD8$^+$ T cells demonstrated killing of SEA-C215 treated C215$^+$ colon carcinoma cells, but did not lyse SEA treated cells. The interaction of T cells with SEA-C215 mAb conjugate bound to MHC Class II tumor cell seems to involve interaction with specific V-beta TCR sequences in a similar manner as earlier demonstrated for SEA induced killing of MHC Class II$^+$ cells. This was indicated by the interaction of an SEA specific but not an autologous SEB specific T cell line with the C215-SEA conjugate. C242 mAb and Thy-1.2 mAb conjugates demonstrate activity in analogy with the C215 mAb conjugate.

Chromium Labelling and Incubation of the Target Cells with SEA 0.75x10$^6$ target cells and 150 $\mu$Ci $^{51}$chromium (Amersham Corp., Arlington Hights, England) were incubated for 45 minutes at 37° C. in a volume of 100 $\mu$l. The cells were kept in complete medium containing RPMI-1640 medium (Gibco, Paisley, GBR) supplemented with 2.8% (v/v) 7.5% $NaHCO_3$, 1% sodium pyrovate, 2% 200 mM L-glutamine, 1% 1M Hepes, 1% 10 mg/ml gentamicin and 10% fetal calf serum (FCS, Gibco, Paisley, GBR). After the incubation the cells were washed once in complete medium without FCS and incubated 60 minutes at 37° C. and washed and resuspended in complete medium containing 10% FCS. 5x10$^3$ target cells were added to each well of U-bottom 96-well microtiter plates (Costar, Cambridge, USA).

Cytotoxicity Assay

The effector cells were added to the wells at various effector/target cell ratios. The final volume in each well was 200 $\mu$l. Each test was done in triplicate. The plates were incubated 4 hours at 37° C. after which the released chromium was harvested. The amount $^{51}$Cr was determined in a gamma-counter (Cobra Auto-gamma, Packard). The percentage cytotoxicity was computed by the formula % cytotoxicity=(X−M)/(T−M) * 100, where X is the chromium release as cpm obtained in the test sample, M is the spontaneous chromium release of target cells incubated with medium, and T is the total chromium release obtained by incubating the target cells with 1% sodium dodecyl sulfate.

RESULTS

SEA-C242, SEA-C215 and SEA-anti-Thy-1.2 mAb conjugates bind to cells expressing the relevant epitopes of the mAbs, respectively, and to MHC Class II$^+$ cells. Unconjugated SEA on the other hand only binds to MHC Class II$^+$ cells. Unconjugated C215, C242 and Thy-1.2 mAbs bind to the relevant cells but not to Raji cells. (Table 1)

Human T cell lines lysed the MHC Class II$^-$ SW620, Colo205 and WiDr cells in the presence of SEA-C215 mAb conjugate but not in the presence of unconjugated SEA and C215 mAb (FIG. 1). The lysis of colon carcinoma cells was seen at 10–100 ng/ml of SEA-C215 mAb conjugate. High levels of lysis at various effector to target ratios were seen with SEA-215 mAb conjugate against SW620 (FIG. 1). In contrast, unconjugated SEA or C215 mAb mediated no cytotoxicity against SW620 cells at all tested effector to target ratios. This indicates that the capacity to lyse MHC Class II$^-$ Colo205 cells is restricted to the conjugate and cannot be induced by unconjugated SEA and C215 mAb. SEA and SEA-C215 mAb conjugate but not C215 mAb mediated T cell killing of MHC Class II$^+$ Raji cells and of interferon treated MHC Class II$^+$ Colo205 cells (FIG. 1).

Figure 2:
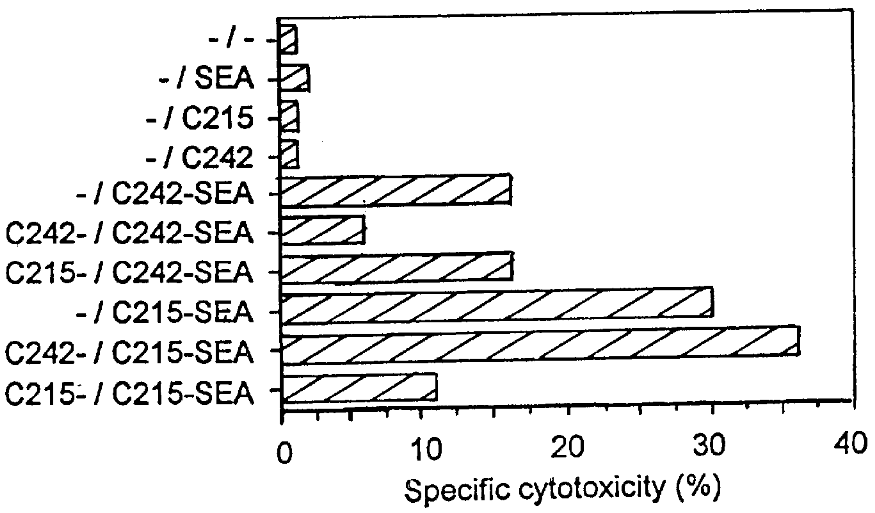
FIG. 2 shows SEA-C215 mAb conjugate and SEA-C242 mAb conjugate induced CTL targeting against colon carcinoma cells.

In order to demonstrate that the SEA-C215 mAb conjugate mediated lysis involved specific binding of the conjugate to the C215 mAb molecule on the target cells, we performed blocking studies with excess of unconjugated C215 mAb and mAb C242, which bind to an irrelevant antigen on the colon carcinoma cells (in regard to C215 mAb binding). Addition of mAb C215 strongly blocked cytotoxicity, whereas the C242 mAb had no influence (FIG. 2). Similarly lysis by a SEA-C242 mAb conjugate was specifically blocked by excess of unconjugated C242 mAb but not C215 mAb.

The capacity of SEA-C215 mAb conjugate to induce T cell dependent lysis of MHC Class II SW620 colon carcinoma cells was seen in both CD4$^+$ and CD8$^+$ T cell populations (Table 2). SEA did not activate any of these T cell subsets to mediate killing of SW620 cells but induced lysis of MHC Class II$^+$ Raji cells (Table 2).

Figure 3A:
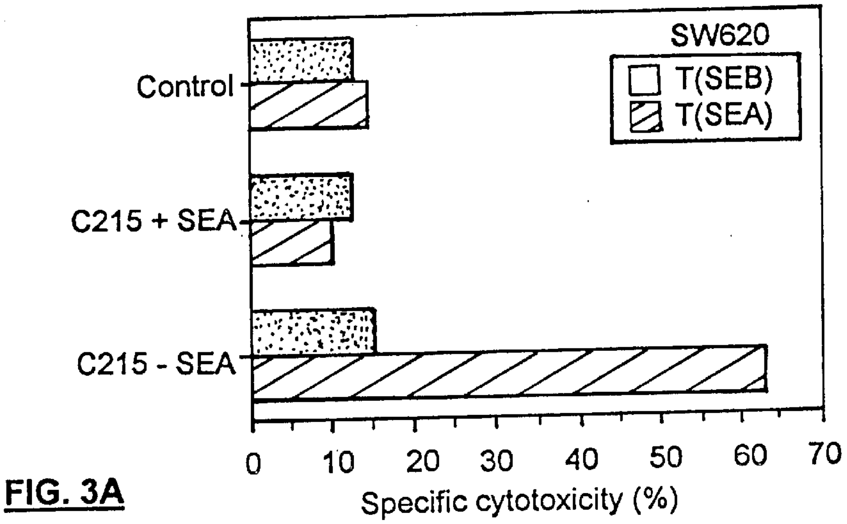
FIG. 3 shows lysis of SEA-C215 mAb conjugate coated colon carcinoma cells mediated by SEA but not SEB responding CTLs.
Figure 3B:
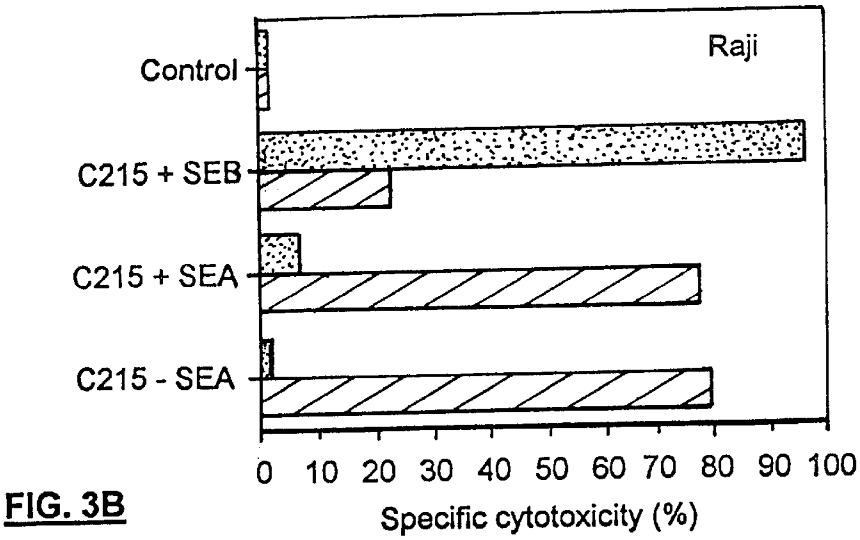
Figure 4A:
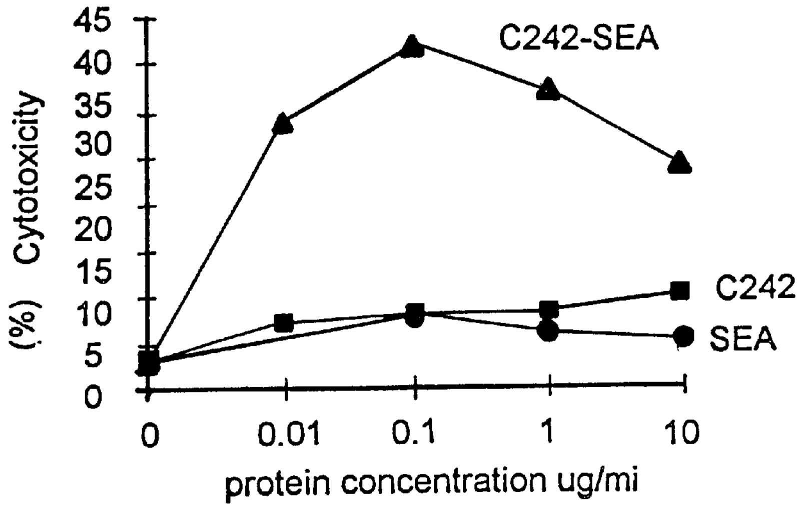
FIG. 4 shows cytotoxicity induced by SEA-C242 mAb conjugate and SEA-Anti-Thy-1.2 mAb conjugate against target cells.
Figure 4B:
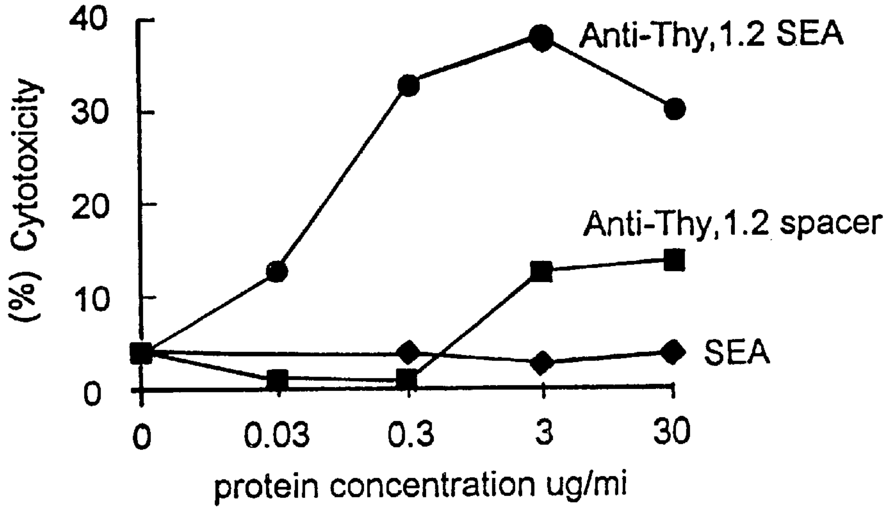

The SEA-C215 mAb conjugate induced lysis of SW620 and Raji cells by a SEA expanded T cell line, but not by a SEB expanded T cell line (FIG. 3). The specificity of the SEA and SEB lines is indicated by their selective response to SEA and SEB, respectively, when exposed to Raji cells (FIG. 4). This indicates that the SEA-C215 mAb conjugate retains similar V-beta TCR specificity as for unconjugated SEA.

Legend to Figures

FIG. 1. The SEA-C215 mAb conjugate directs CTLs against MHC class II$^-$ colon carcinoma cells. Upper left panel demonstrates the effect of SEA responsive CTLs against SW620 cells at various effector to target ratios in the absence (−) or presence of SEA-C215 mAb conjugate, SEA, C215 and a mixture of C215 and SEA (C215+SEA) at a concentration of 1 $\mu$g/ml of each additive. The other panels demonstrates the capacity of SEA-C215 mAb conjugate, and SEA to target SEA responsive CTLs against the C215+ MHC class II$^-$ colon carcinoma cell lines SW620, Colo205 and WiDr, MHC class II$^+$ C215$^+$ interferon treated Colo205 cells and C215-MHC class II$^+$ Raji cells. Effector to target ratio was 30:1. Addition of unconjugated C215 mAb, at several concentrations, did not induce any CTL targeting against these cell lines. FACS analysis on SW620 cells, Colo205 and WiDr cells using mAbs against HLA-DR, −DP, −DQ failed to detect any surface MHC class II expression, whereas abundant expression of HLA-DR, −DP and −DQ was detected on Raji cells and HLA-DR and −DP on interferon treated Colo205 cells. Colo205 cells were treated with 1000 units/ml of recombinant interferon-gamma for 48 hours prior to use in the CTL assay.

FIG. 2. SEA-C215 mAb conjugate and SEA-C242 mAb conjugate induced CTL targeting against colon carcinoma cells depends on the antigen selectivity of the mAb. Lysis of Colo205 cells by a SEA responsive CTL line in the presence of SEA-C215 mAb and SEA-C242 mAb conjugate (3 μg/ml) is blocked by addition of unconjugated C215 and C242 mAbs (30 μg/ml), respectively. The unconjugated mAbs or control medium (−) were added to the target cells 10 minutes prior to the conjugates.

FIG. 3. Lysis of SEA-C215 mAb conjugate coated colon carcinoma cells is mediated by SEA but not SEB responding CTLs. Autologous SEA and SEB selective T cell lines were used at an effector to target ratio of 10:1 against SW620 and Raji target cells in the absence (control) or presence of SEA-C215 mAb conjugate, a mixture of unconjugated C215 mAb and SEA (C215+SEA) and unconjugated C215 mAb and SEB (C215+SEB) at a concentration of 1 μg/ml of each additive.

FIG. 4. Cytotoxicity induced by the SEA-C242 mAb conjugate and SEA-Anti-Thy-1.2 mAb conjugate against their target cells (Colo205 tumour cells and EL-4 tumour cells, respectively).

TABLE 1

SEA-C215 mAb conjugate bind to $C215^+$ colon carcinoma cells and MHC Class $II^+$ Raji cells

| Reagent | Cell | Facs analysis |
|---|---|---|
| SEA-C215 mAb | Colo205 | Pos |
| | Raji | Pos |
| C215 mAb | Colo205 | Pos |
| | Raji | Neg |
| SEA-C242 mAb | Colo205 | Pos |
| | Raji | Pos |
| C242 mAb | Colo205 | Pos |
| | Raji | Neg |
| SEA-anti-Thy-1.2 mAb | EL-4 | Pos |
| anti-Thy-1.2 mAb | EL-4 | Pos |
| SEA | Colo205 | Neg |
| | Raji | Pos |
| control | Colo205 | Neg |
| | Raji | Neg |
| | EL-4 | Neg |

Cells were incubated with the various additives of control (PBS-BSA) for 30 minutes on ice, washed and processed as described below. The staining of C215 mAb and C242 mAb bound to Colo205 cells and anti-Thy-1.2 bound to EL-4 cells was detected using FITC labelled rabbit anti mouse 1 g. The staining of SEA to Raji cells was detected using a rabbit anti-SEA sera followed by a FITC-swine anti rabbit 1 g. The staining of SEA-C215 mAb conjugate to Colo 205 and Raji cells was detected utilizing the above described procedures for C215 mAb and SEA. FACS analysis was performed on a FACS star plus from Becton and Dickinson. Staining with second and third steps only was utilized to define the background.

TABLE 2

$CD4^+$ and $CD8^+$ CTLs lyse colon carcinoma cells presenting the C215-SEA conjugate

| | | % cytotoxicity | | |
|---|---|---|---|---|
| Effector[A)] | Target | control | SEA | C215-SEA |
| $CD4^+$ | SW620 | 2 | 5 | 50 |
| $CD4^+$ | Raji | 0 | 41 | 43 |
| $CD8^+$ | SW620 | 0 | 1 | 23 |
| $CD8^+$ | Raji | 2 | 72 | 68 |

[A)]The CTLs (SEA-3) were used at effector to target ratios of 30:1 in the absence (control) or presence of SEA and C215-SEA at 1 μg/ml.

What is claimed is:

1. A soluble antibody conjugate comprising a superantigen covalently linked by peptide bond linkage to an antibody, wherein said antibody is specific for a cell surface structure on a cell, said superantigen is recognized by T-cells and capable of activating cytotoxic T-cells (CTLs), and said conjugate has been produced using recombinant techniques.

2. A conjugate according to claim 1, wherein said cell is associated with disease selected from the group consisting of cancer, autoimmunity, parasitic infestation, and microbial infections.

3. A conjugate according to claim 1, wherein said cell is associated with cancer.

4. A conjugate according to claim 3, wherein said cell is a colon carcinoma.

5. A conjugate according to claim 1, wherein said cell surface structure is a C242 epitope.

6. A conjugate according to claim 1, wherein the superantigen is of bacterial origin.

7. A conjugate according to claim 6, wherein the superantigen is SEA.

8. A conjugate according to claim 1, wherein said cell surface structure is a C242 epitope and the superantigen is SEA.

9. A method for the treatment of a mammal, including a human individual, suffering from a disease selected from the group consisting of cancer; autoimmunity; an infection caused by a virus; a bacteria or fungi; and an infestation caused by a parasite; said method comprising administering to said mammal a target cell lysis effective amount of a conjugate according to claim 1.

10. A method according to claim 9, wherein said disease is cancer.

11. A method according to claim 10, wherein said cancer is colon carcinoma.

12. A method according to claim 9, wherein said cell surface structure is a C242 epitope.

13. A method according to claim 9, wherein the superantigen is of bacterial origin.

14. A method according to claim 13, wherein the superantigen is SEA.

15. A method according to claim 9, wherein said cell surface structure is a C242 epitope and the superantigen is SEA.

16. A method for the lysis of a target cell by assistance of T-cells, wherein the target cell is contacted with a target cell lysis effective amount of a soluble antibody conjugate comprising a monoclonal antibody or antibody fragment covalently linked by peptide bond linkage to a superantigen, and said conjugate has been produced using recombinant techniques; wherein said monoclonal antibody or antibody fragment is specific for a cell surface structure on said target cell, and said superantigen is recognized by the T-cells and capable of activating cytotoxic T-Cells (CTLs).

17. A method according to claim 16, wherein said target cell is associated with disease selected from the group consisting of cancer, autoimmunity, parasitic infestation, and microbial infections.

18. A method according to claim 16, wherein said target cell is associated with cancer.

19. A method according to claim 18, wherein said cell is a colon carcinoma.

20. A method according to claim 16, wherein said cell surface structure is a C242 epitope.

21. A method according to claim 16, wherein the superantigen is of bacterial origin.

22. A method according to claim 21, wherein the superantigen is SEA.

23. A method according to claim 16, wherein said cell surface structure is a C242 epitope and the superantigen is SEA.

24. A conjugate substance comprising individual soluble conjugates, wherein each individual conjugate comprises a superantigen covalently linked by peptide bond linkage to an antibody, wherein said antibody is specific for a cell surface structure on a cell, said superantigen is recognized by T-cells and capable of activating cytotoxic T-cells (CTLs), and said conjugate has been produced using recombinant techniques, and wherein the all individual conjugate molecules in the conjugate substance are uniform with regard to the number of superantigens per antibody, and with regard to the covalent linkage between the antibody and superantigen.

25. The plurality of conjugates according to claim 24, wherein said cell surface structure is a C242 epitope and the superantigen is SEA.

26. A method for the treatment of a mammal, including a human individual, suffering from a disease selected from the group consisting of cancer; autoimmunity; an infection caused by a virus; a bacteria or fungi; and an infestation caused by a parasite; said method comprising administering to said mammal a target cell lysis effective amount of the conjugate substance of claim 24.

27. A method according to claim 26, wherein said disease is cancer.

28. A method according to claim 27, wherein said cancer is colon carcinoma.

29. A method according to claim 26, wherein said cell surface structure is a C242 epitope.

30. A method according to claim 26, wherein the superantigen is of bacterial origin.

31. A method according to claim 30, wherein the superantigen is SEA.

32. A method according to claim 26, wherein said cell surface structure is a C242 epitope and the superantigen is SEA.

* * * * *